United States Patent
Koehl et al.

(10) Patent No.: US 11,530,964 B2
(45) Date of Patent: Dec. 20, 2022

(54) FLUID SENSOR SYSTEM AND METHOD FOR ANALYSING FLUID

(71) Applicants: OWLSTONE MEDICAL LIMITED, Cambridge (GB); OWLSTONE INC., Westport, CT (US)

(72) Inventors: Andrew H. Koehl, Cambridge (GB); Max Allsworth, Essex (GB)

(73) Assignees: OWLSTONE MEDCIAL LIMITED, Cambridge (GB); OWLSTONE INC., Westport, CT (US)

( * ) Notice: Subject to any disclaimer, the term of this patent is extended or adjusted under 35 U.S.C. 154(b) by 370 days.

(21) Appl. No.: 16/637,356

(22) PCT Filed: Aug. 7, 2018

(86) PCT No.: PCT/GB2018/052246
§ 371 (c)(1),
(2) Date: Feb. 7, 2020

(87) PCT Pub. No.: WO2019/030510
PCT Pub. Date: Feb. 14, 2019

(65) Prior Publication Data
US 2021/0055186 A1      Feb. 25, 2021

(30) Foreign Application Priority Data
Aug. 8, 2017   (GB) .................................... 1712712

(51) Int. Cl.
*B01D 53/04* (2006.01)
*G01N 1/34* (2006.01)
(Continued)

(52) U.S. Cl.
CPC ....... *G01N 1/2214* (2013.01); *B01D 53/0438* (2013.01); *B01D 53/261* (2013.01);
(Continued)

(58) Field of Classification Search
CPC .. B01D 53/04; B01D 53/0438; B01D 53/261; B01D 2253/102; B01D 2253/108;
(Continued)

(56) References Cited

U.S. PATENT DOCUMENTS

| 4,786,472 A | 11/1988 | McConnell et al. |
| 5,952,652 A | 9/1999 | Taylor et al. |

(Continued)

FOREIGN PATENT DOCUMENTS

WO     93/06476 A1    4/1993

OTHER PUBLICATIONS

"Written Opinion of the International Searching Authority," PCT/GB2018/052246, European Patent Office, Munich, Germany, dated Dec. 11, 2018.

*Primary Examiner* — Frank M Lawrence, Jr.
(74) *Attorney, Agent, or Firm* — Leveque Intellectual Property Law, P.C.

(57) ABSTRACT

A sensor system comprising a housing having an inlet aperture through which fluid enters the housing and a conditioning material in the housing, the conditioning material being adapted to control levels of a substance within the housing. The sensor system comprises a sensor for analysing the fluid in the housing. The sensor system comprises circulation means which is configured to alternate circulation of fluid within the housing between a sensing fluid path in which the fluid is analysed by the sensor and a second fluid path in which the fluid flow is conditioned. A method for analysing fluid in a housing using a sensor is also provided.

19 Claims, 8 Drawing Sheets

(51) Int. Cl.
  *G01N 1/22* (2006.01)
  *B01D 53/26* (2006.01)
  *G01N 1/40* (2006.01)
  *G01N 27/622* (2021.01)
  *G01N 33/00* (2006.01)
  *G05D 7/01* (2006.01)

(52) U.S. Cl.
  CPC ............ *G01N 1/405* (2013.01); *G01N 27/622* (2013.01); *G01N 33/006* (2013.01); *G05D 7/01* (2013.01); *B01D 2257/80* (2013.01)

(58) Field of Classification Search
  CPC .... B01D 2257/80; G01N 1/2214; G01N 1/34; G01N 1/405; G01N 27/622; G01N 33/006; G05D 7/01
  USPC .............. 96/108, 111, 146, 413; 95/8–11, 90
  See application file for complete search history.

(56) References Cited

U.S. PATENT DOCUMENTS

| | | | |
|---|---|---|---|
| 6,288,400 | B1 | 9/2001 | Negro |
| 6,455,003 | B1* | 9/2002 | Anvia ...................... G01N 1/40 436/178 |
| 2008/0066619 | A1 | 3/2008 | Petinarides |
| 2011/0303024 | A1 | 12/2011 | Wallis et al. |
| 2012/0068061 | A1* | 3/2012 | Griffin ................. G01N 27/622 250/282 |
| 2012/0270334 | A1 | 10/2012 | Ojeda et al. |
| 2013/0234013 | A1 | 9/2013 | Patterson et al. |
| 2019/0250073 | A1* | 8/2019 | Makino ................... G01N 1/44 |

\* cited by examiner

FLUID SENSOR SYSTEM AND METHOD FOR ANALYSING FLUID

TECHNICAL FIELD

The invention relates to a sensor system, for example but not exclusively electrochemical sensors or field asymmetric ion mobility spectrometry sensors.

BACKGROUND

There are a wide range of sensors, for example electrochemical sensors or field asymmetric ion mobility spectroscopy (FAIMS), which are used to detect particular chemicals within gases such as air. Humidity is a factor that affects the performance of such sensors, particularly those operating in air. The humidity in such a sensor system is often controlled actively using relatively costly and large hardware.

U.S. Pat. No. 5,952,652 describes an ion mobility spectrometer which includes a vapour absorbent material held in close proximity with an ion mobility spectrometer cell within a housing. This provides the possibility of constructing a miniature instrument without the need for any external air supply. WO93/06476 describes ion mobility spectrometry equipment comprising an enclosed compartment contained within which there is an IMS cell and a body of absorbent material. Samples are drawn into the compartment through a pinhole by a negative pressure pulse produced by a loudspeaker. US2013/0234013A1 describes a detection system including a housing having a sample port, a detector assembly and a pump in flow communication with the detector assembly. A dryer cartridge is removably coupled to an outer surface of the housing of the detector system.

U.S. Pat. No. 4,786,472 describes a briefcase containing components capable of sampling air for analysis. Air is introduced through inlet ports and air can be monitored for components of environmental tobacco smoke using various detectors. U.S. Pat. No. 6,288,400 describes a portable radometer having a pump which pulls air through a desiccant filter into a sampling chamber to a detector.

The applicant has also recognised the need for a lower cost solution with a reasonable lifespan.

SUMMARY

According to the present invention there is provided an apparatus and method as set forth in the appended claims. Other features of the invention will be apparent from the dependent claims, and the description which follows.

According to one embodiment, there is provided a sensor system comprising a housing having an inlet aperture through which fluid enters the housing; a conditioning material in the housing, the conditioning material being adapted to control levels of a particular substance within the housing; a sensor for analysing the fluid in the housing; and circulation means which is configured to alternate circulation of fluid within the housing between a sensing fluid path in which the fluid is analysed by the sensor and a second fluid path in which the fluid flow is conditioned using the conditioning material.

The conditioning material conditions the fluid by changing its properties, e.g. to increase or decrease the amount of another substance within the fluid. For example, the conditioning material may be a sorbent, i.e. any suitable material which adsorbs or absorbs the particular substance, typically water, from the fluid. Suitable examples include activated carbon such as that used by Restek Corporation in its products or a molecular sieve material (e.g. 13× molecular sieve). When controlling levels of water, the sorbent material may be controlling humidity within the housing. Alternatively, the conditioning material may increase the levels of the substance in the housing. For example, the conditioning material may release water into the housing which increases humidity or the conditioning material may add a modifier gas into the housing.

The second fluid path may be a drying path in which the fluid is dried by the conditioning material (i.e. by a sorbent material which absorbs or adsorbs the substance). The conditioning material may be located in the housing so that fluid flows through the sorbent in the drying path. In other words, the conditioning material may be located in the drying path. Alternatively, the conditioning material may be located in the housing so that the conditioning material is not in a fluid path and there is diffusive drying in the drying path. Where there is a separate drying path, the conditioning material may be located in the housing outside the sensing fluid path so that the fluid does not flow through the conditioning material when analysis of the fluid is occurring.

The housing may comprises an exit aperture through which fluid exits the housing. The second fluid path may be a regeneration path with fluid flow through the exit aperture. For example, the exit aperture may have an area in the range of between 1 $\mu m^2$ to 1 $mm^2$. The exit aperture may be used to allow the system to stabilise to ambient pressure. In such an arrangement, the exit aperture is preferably about ten times smaller than the inlet aperture. In this way, in the arrangement when the pump is turned on to draw in a fluid sample, the fluid sample is drawn through the inlet aperture rather than through the exit aperture.

The conditioning material may be located in the housing so that when fluid flows through the regeneration path, the fluid may also flow through the conditioning material. Fluid may also flow through the conditioning material in the sensing path. The conditioning material may be a sorbent and during regeneration, any substances, e.g. water, which have been adsorbed or absorbed by the sorbent material, e.g. when fluid is flowing in the sensing path, are purged. A heat source may be in thermal contact with the sorbent material to purge the sorbent material of adsorbed or absorbed species. The heat source may comprise a heating element. The heating element may be in direct contact with the sorbent material.

The circulation means may be any suitable device for circulating flow within the housing, e.g. a pump, fan or transducer. The circulation means may be configured for bi-directional operation whereby altering the direction of operation of the circulation means alternates circulation of fluid within the housing between the sensing fluid path and the second fluid path. In other words, when the circulation means is operating in one direction, the fluid flows in the sensing fluid path and when the circulation means is operating in the opposite direction, the fluid flows in the second fluid path. The circulation means may be configured to pulse between directions, particularly between when the second fluid path is the regeneration path. Alternatively, the circulation means may be configured to alternate circulation of fluid by switching to a rest phase to circulate fluid in the second fluid path, e.g. when there is a diffusive drying in the drying path.

The circulation means may also be a membrane on the inlet, the membrane having a variable diffusion rate. For example the diffusion rate may be temperature dependent such that at a first temperature, the diffusion rate may be high so that the fluid flows in the sensing fluid path and at a second temperature, the diffusion rate may be low so that the fluid flows in the conditioning fluid path. In such an arrangement, the circulation means may be the membrane. The housing may have a conditioning chamber within which the conditioning material is located. In such an arrangement, the circulation means may be a variable diffusion rate membrane, a controllable valve and/or a diffusion limited aperture into the conditioning chamber whereby the membrane, valve or aperture control the rate of diffusion into the conditioning chamber and hence in the second fluid path. Alternatively, the circulation means may be a mechanism for varying the size of the conditioning chamber which controls the rate of diffusion into the conditioning chamber and hence in the second fluid path.

Alternatively or additionally, the rate of flow into the conditioning chamber may be controlled by the use of a valve or a membrane 612 over the aperture into the conditioning chamber or by the use of a diffusion limited aperture (pinhole aperture). For example, the membrane may have a variable diffusion rate depending on its temperature so that at a first temperature, the diffusion rate may be high so that the fluid flows in the circulation fluid path and at a second temperature, the diffusion rate may be low so that the fluid flows in the sensing fluid path. In such an arrangement, the circulation means may be the valve, conditioning chamber valve, membrane and/or aperture. The shape of the conditioning chamber may also be used to control the diffusion rate, for example the size of the chamber may be variable to increase or decrease the distance from the inlet to the sorbent to adjust the diffusion rate to the sorbent. For example, at a first shorter length, the diffusion rate may be high so that the fluid flows in the circulation fluid path and at a second longer length, the diffusion rate may be low so that the fluid flows in the sensing fluid path. In such an arrangement, the circulation means may be the mechanism controlling the shape of the conditioning chamber.

Alternatively or additionally, the rate of flow may be adjusted by changing the distance between the inlet and the sensor. For example, at a first shorter length, the diffusion rate may be high so that the fluid flows in the sensing fluid path and at a second longer length, the diffusion rate may be low so that the fluid flows in the conditioning fluid path. In such an arrangement, the circulation means may be the mechanism controlling the distance between the inlet and the sensor.

The inlet aperture may be small, i.e. its size may be small relative to the size of the housing. For example, the inlet aperture may have a size in the range of 1 μm$^2$ to 1 mm$^2$. The sensor system may comprise an inlet valve to control flow through the inlet aperture. Similarly, the exit aperture may have an exit valve to control flow through the exit aperture. The circulation means and the inlet valve and/or the exit valve may be co-operatively configured so that operation of the circulation means controls the opening and closing of the inlet or exit valve. For example, the circulation means may be configured to cause a pressure change within the housing so that there is a increase in the magnitude of the pressure differential between the pressure within the housing ($P_1$) and the external pressure ($P_2$). The pressure differential may be defined as:

$$\Delta P = P_1 - P_2$$

When the magnitude of the pressure differential is above a threshold rate, the inlet valve may be opened to allow fluid flow into the housing. When the circulation means is causing the magnitude of the pressure differential to be above the threshold rate, this may be termed a loading phase. The threshold rate may be of the order of 10 to 100 mbar. As explained below, driving the circulations means may reduce the pressure within the housing which draws open the inlet valve. The circulation means may be configured to operate so that the magnitude of the pressure differential is below the threshold rate whereby the inlet valve is closed. The circulation means may be configured to operate below the threshold rate when alternating fluid between the sensing path and the second fluid path. In other words, fluid is only loaded into the housing when the circulation means is operating above the threshold value.

The sensor and/or the circulation means may be located in the housing. The housing may comprise at least two internal chambers. For example, the housing may comprise a flow chamber which houses the pump and a second chamber which houses the sensor. There may be a first internal aperture between the flow chamber and the second chamber. The second chamber may also house the conditioning material. Alternatively, the second chamber is a sensing chamber and the housing further comprises a drying chamber which houses the conditioning material, e.g. sorbent. In other words, the sorbent is separated from the sensing chamber. The system may comprise a second internal aperture between the flow chamber and the sensing chamber and a third internal aperture between the drying chamber and the sensing chamber. The second internal aperture may be an exit aperture to allow fluid to exit the drying chamber and the third internal aperture may be an inlet aperture to allow fluid to enter the drying chamber. In operation, fluid may flow through the second internal aperture but not the third internal aperture in the sensing fluid path and fluid may flow through the third internal aperture but not the second internal aperture in the second fluid path.

The size of some or all of the internal apertures may be small relative to the overall size of the chamber to control flow therethrough. Internal valves, e.g. one-way valves, may be further added to control flow through the internal apertures. For example internal valves may be used on the second and third internal apertures. The circulation means may be configured to control opening and closing of the internal valves. For example, circulation means may be configured for bi-directional operation whereby altering the direction of operation of the circulation means alternates which of the internal valves is opened and closed.

In the first fluid path, the fluid may flow through or past the sensor to be analysed. The sensor may be any suitable detector for analysing the fluid. For example, the sensor may be a FAIMS sensor, i.e. a sensor which may be used to distinguish charged gaseous molecules according to differences in the speed that the molecules move through a buffer gas under the influence of an oscillating electric field. The circulation means may be in direct fluid connection with the sensor. The fluid may flow through the sensor multiple times when the fluid is flowing in the sensing fluid path and thus the sensor may be configured to analyse the fluid using averaging techniques.

There is also described a method for analysing fluid in a housing using a sensor, the method comprising: drawing fluid into the housing through an inlet aperture; selecting a fluid path within the housing wherein the fluid path is selected from a sensing path in which fluid flows through the sensor to be analysed and a second fluid path which is separate from the first fluid path; circulating the fluid within the selected fluid path using circulation means located within the housing; analysing the fluid within the housing using the sensor when the fluid is flowing in the sensing path; and controlling a level of a substance with the fluid using a conditioning material located within the housing when the fluid is flowing in the second fluid path.

The second fluid path may be a drying path and controlling the level of the substance may comprise removing the unwanted substance by drying the fluid, e.g. using a sorbent material. Alternatively, the second fluid path may be a regeneration path and controlling the level of the substance may comprise removing the unwanted substance by opening an exit aperture to permit fluid flow through the exit aperture. Where a sorbent material is used, the method may comprise heating the sorbent material when the fluid is flowing in the regeneration path to remove adsorbed or absorbed substance from the sorbent material. In other words, when the second fluid path is a regeneration path, the method may comprise drying (or otherwise removing the substance) when the fluid is flowing in the sensing path. By contrast, when there is a separate drying path, there may be no drying when the fluid is flowing in the sensing path. Alternatively, controlling the level of the substance may comprise adding the substance into the housing. As set out above, the conditioning material may be any suitable material.

The method may comprise drawing fluid into the housing before the other steps are carried out. For example, the method may comprise drawing fluid into the housing by opening an inlet valve on the inlet aperture and closing the inlet valve before selecting the fluid path. Opening the inlet valve may be achieved by operating the circulation means so that the magnitude of the pressure differential between the pressure within the housing and the pressure external to the housing is above a threshold rate. This effectively reduces the pressure within the housing and opens the valve. Opening the inlet valve may be for a short burst, e.g. between 0.5 seconds to a few, e.g. five, seconds.

The circulation means may be configured for bi-direction operation. The method may comprise circulating the fluid within the selected fluid path by selecting a direction of operation of the circulation means which drives the fluid in the selected fluid path. Alternatively, or additionally, circulating the fluid within the second fluid path may comprises operating the circulation means in a rest phase (e.g. if not bi-directional). As explained above, the rest phase allows diffusive drying.

The method may comprise circulating the fluid in the second fluid path before circulating the fluid in the sensing path or vice versa or alternating between the two paths as required. The method may comprise analysing the fluid using averaging techniques. This is particular successful if the fluid can be circulated multiple times in the sensing path and also if the fluid remains the same, i.e. does not pass through the sorbent material whilst averaging is being used. The conditioning material may be housed in a conditioning chamber within the housing and the system comprises an internal valve on the conditioning chamber. The method further comprise opening the internal valve using the circulation means to circulate fluid in the second fluid path.

BRIEF DESCRIPTION OF THE DRAWINGS

For a better understanding of the invention, and to show how embodiments of the same may be carried into effect, reference will now be made, by way of example only, to the accompanying diagrammatic drawings in which.

DETAILED DESCRIPTION OF THE DRAWINGS

Figure 1A:
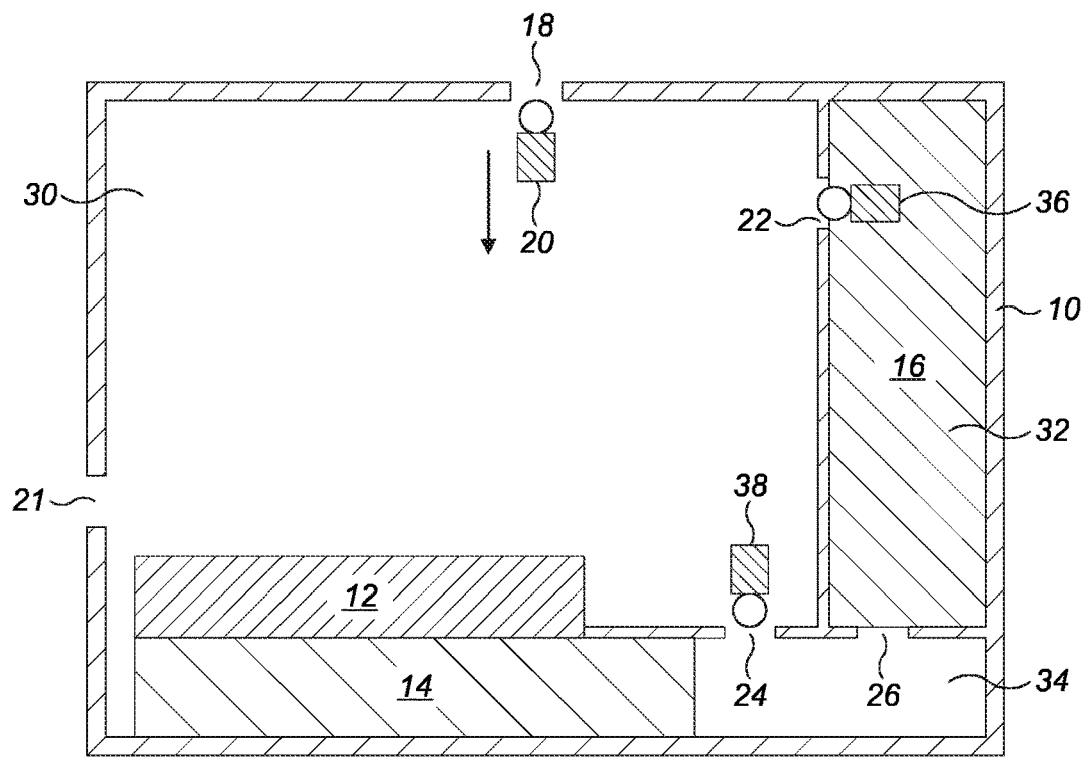
FIGS. 1A to 1C show a first sensor system in three different phases of operation.
Figure 1B:
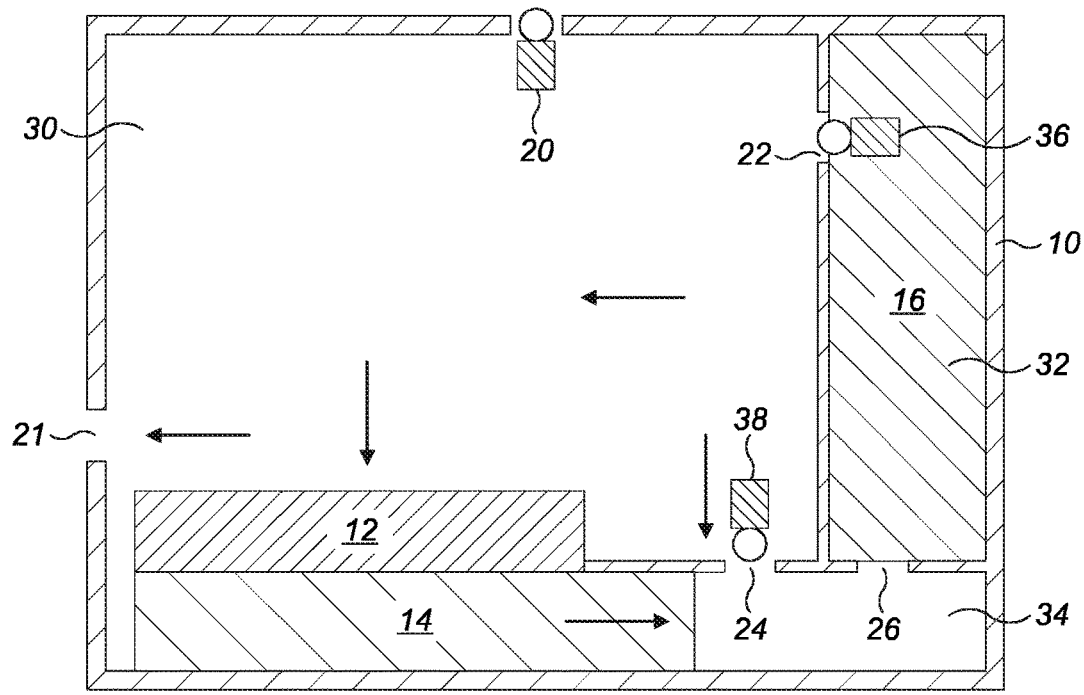
Figure 1C:
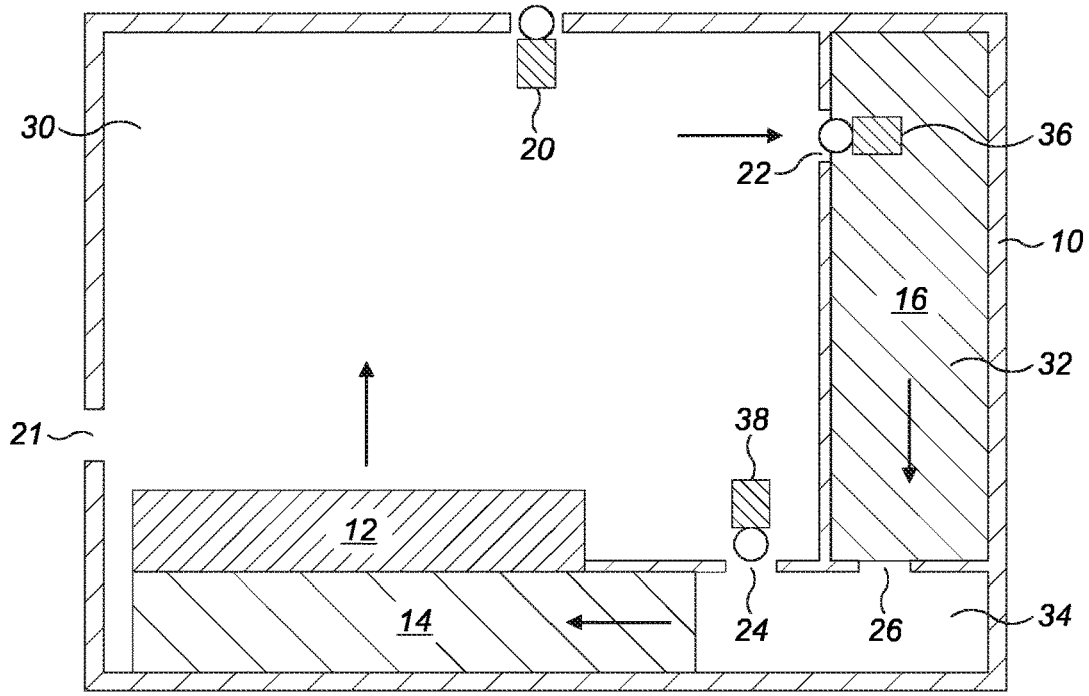

FIGS. 1A to 1C show a first sensor system comprising a housing 10 within which a sensor 12, a pump 14 and a sorbent 16 are located. The sensor may be any suitable sensor or detector which is used to detect the presence of particular chemicals within fluids such as an air. Examples of suitable sensors include an electrochemical sensor or a field asymmetric ion mobility spectroscopy (FAIMS) sensor. Similarly, the sorbent 16 may be any suitable material, which removes (by adsorption or absorption) unwanted substances from the fluid sample. Typically the sorbent 16 will remove water from an air sample. The pump is any suitable circulation mechanism which can be operated to circulate fluid within the housing in two different directions as explained in more detail below.

In this arrangement, the pump 14 is located adjacent the sensor 12 but other relative locations of the pump and the sensor are permitted provided that there is a sealed path between the pump and the sensor. By mounting the sensor and pump adjacent to one another, a sealed fluid path between the two components is formed. Alternatively, the sealed path may not be a direct path, e.g. a baffle could be mounted between the sensor and the pump, e.g. to dull pulsability. Such an indirect sealed path could also be achieved by other arrangements which would be known to the skilled person.

An aperture 18 is located on the housing, for example in one wall of the housing as shown to allow a sample of fluid into the housing to be sensed by the sensor 12. Thus the aperture may be termed an inlet aperture. The aperture 18 is preferably small relative to the size of the housing, e.g. 1 $\mu m^2$ to 1 $mm^2$. Control of fluid flow into the housing is controlled by an external valve 20 as described below. The term external is used to denote the fact that the valve controls flow through the external aperture rather than specifying its location relative to the housing. There is also an exit aperture 21 to allow fluid to exit the housing. The exit aperture 21 allows pressure within the housing to stabilise to ambient pressure. Diffusion of the fluid into the housing may limited when an appropriate aperture is chosen either for the inlet aperture 18 or the exit aperture 21 and such an aperture may be termed a diffusion limited aperture or pinhole aperture.

In this arrangement, the housing 10 comprises three internal chambers: a sensing chamber 30 which houses the sensor 12, a drying chamber 32 which houses the sorbent 16 and a flow chamber 34 which houses the pump 14. There are also three internal apertures to allow flow between different chambers within the housing 10. There is a first internal aperture 26 between the flow chamber 34 and the drying chamber 32, a second internal aperture 24 between the flow chamber 34 and the sensing chamber 30 and a third internal aperture 22 between the sensing chamber 30 and the drying chamber 32. Fluid flow through the third and second apertures 24, 26 can be controlled by respective internal valves 36, 38. There is no internal valve on the first internal aperture but one could optionally be included. Again internal is used to denote the fact that the valves control flow through the apertures within the housing. It will be appreciated that the size of the apertures and valves in the drawings is not to scale.

FIG. 1A shows a loading phase of operation for the sensing system. The pump 14 is set at maximum or at least a high rate to reduce the pressure within the sensing chamber relative to the pressure of the fluid outside the housing so that the magnitude in the pressure differential between the two pressures is above a threshold value. The reduction in pressure is sufficient to cause the external valve 20 to open to allow a fluid sample to enter the housing as indicated by the arrow. In this arrangement, the fluid sample (which is typically ambient air) is drawn into the sensing chamber 30 of the housing 10. Once the required sample has been captured, the pump speed is reduced and the sensing system switches to the measurement phase shown in FIG. 1B. It is noted that as shown in FIG. 1A, internal valve 38 is also drawn open by the reduction of pressure within the sensing chamber 30 but internal valve 36 is configured to remain closed.

As shown in FIG. 1B, the external valve 20 is closed. The pump 14 operates at a lower speed than that used in the loading phase to drive circulation of the fluid within the housing. 10 Internal valve 38 is configured to remain open and thus the fluid flows in a measurement circulation or sensing fluid path through the sensor 12, through the pump 14 and back into the sensing chamber 30 through the open second internal aperture 24. In this measurement phase, the fluid sample can be circulated through the sensor multiple times allowing measurement by averaging techniques. During the measurement phase, fluid may diffuse through the exit aperture 21 over time.

Once sufficient measurements have been captured or after a predefined time interval, the sensor system can be configured to operate in a drying phase as shown in FIG. 1C. In this arrangement, this is achieved by reversing the flow direction for the pump 14. This reduces the pressure in the flow chamber 34 relative to the pressure in the sensing chamber 30 which opens internal valve 36 on the third internal aperture 22 and closes internal valve 38 on the second internal aperture 24. In this drying phase, the fluid flows in a drying circulation path in which the fluid flow is not analysed. The path flows from the sensing chamber 30 through the third internal aperture 22 into the drying chamber 32 and hence through the sorbent 16. The flow continues through the first internal aperture 26 into the flow chamber 34 and back through the sensor 12 into the sensing chamber 30.

It will be appreciated that the drying phase can take place before the measurement phase. Moreover, after the drying phase, the sensing system can return to the sensing phase to obtain further measurements or alternatively, the sensing system can be operated in the loading phase to restart the cycle with a new sample. This selective alternation between loading, sensing and drying phases (in any order) allows thousands of average measurements to be taken during the lifetime of the sensor. For example, the sensor system can be run at a very low duty cycle to achieve perhaps 10 years operation.

Figure 2A:
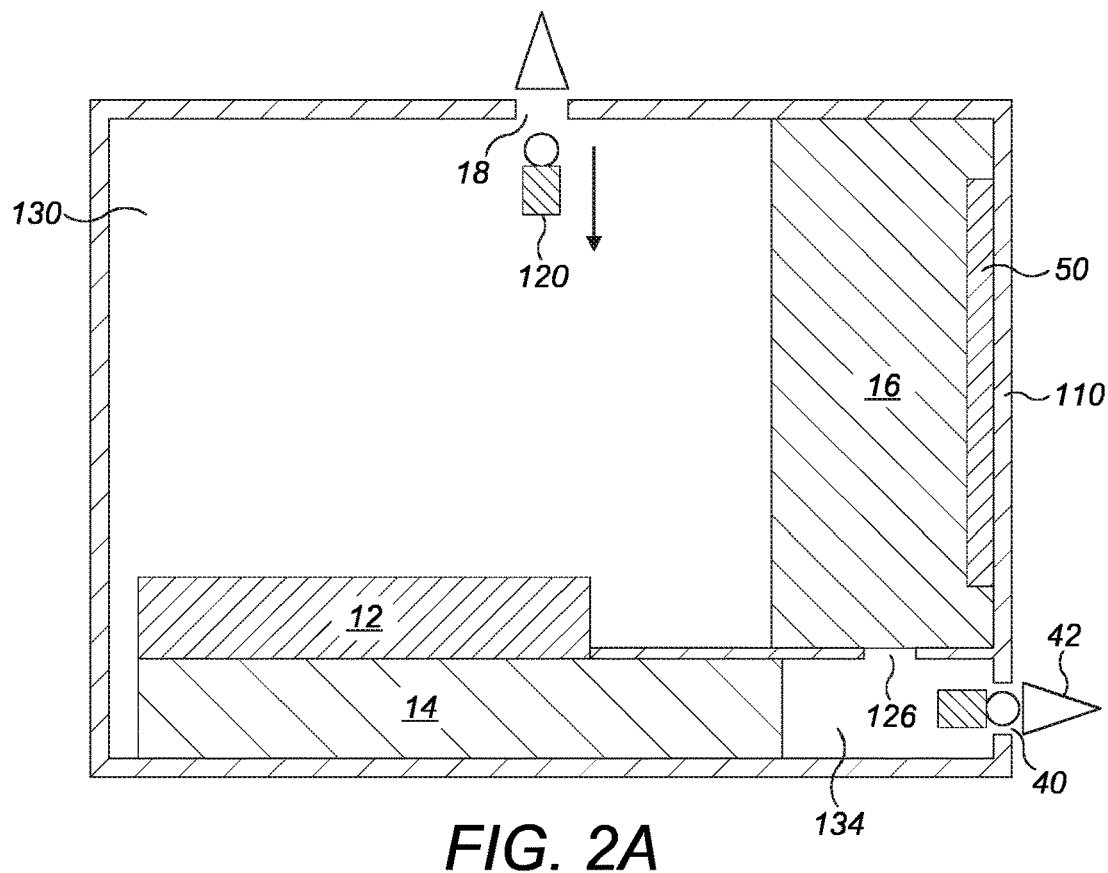
FIGS. 2A to 2C show a second sensor system in three different phases of operation.
Figure 2B:
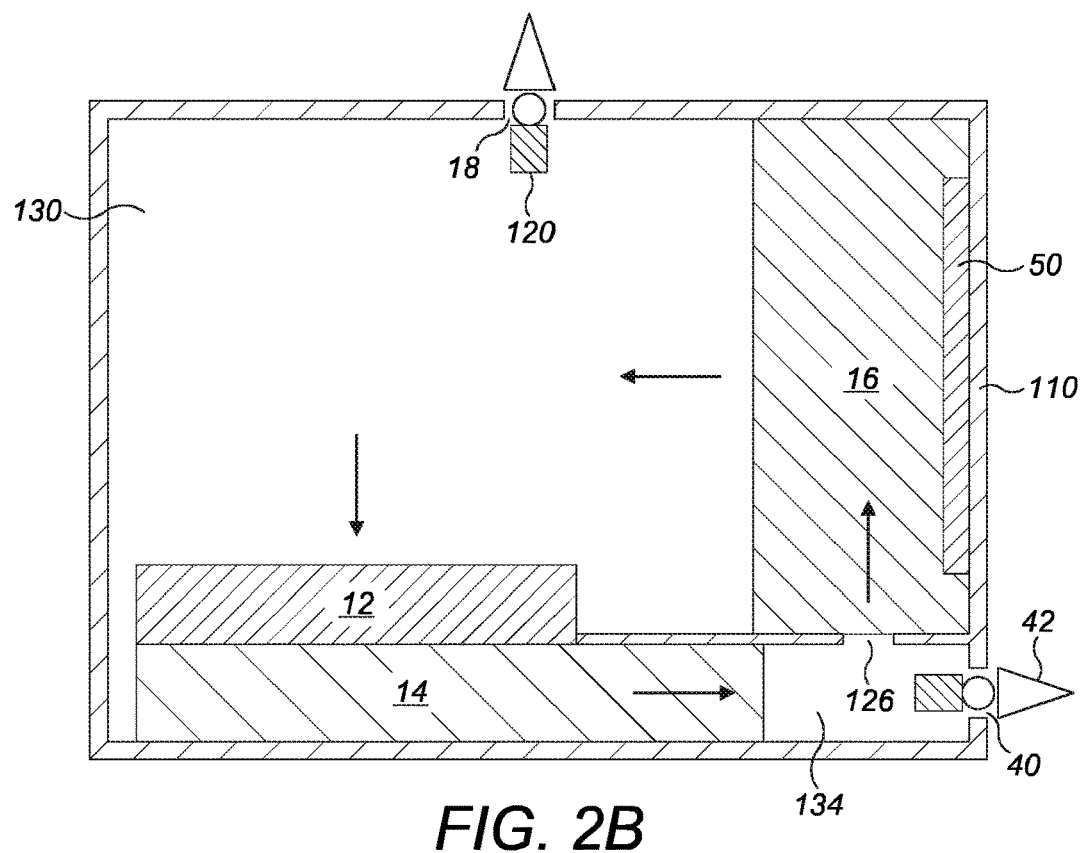
Figure 2C:
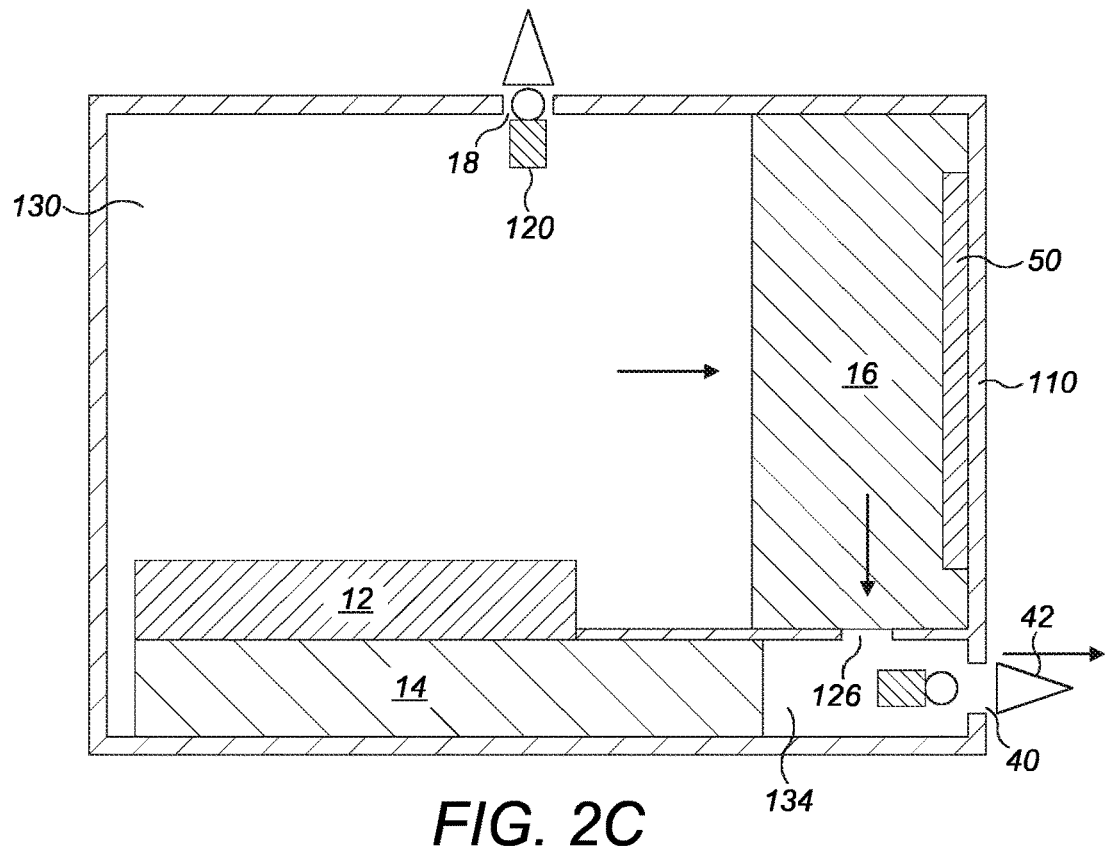

FIGS. 2A to 2C show a second sensor system having many features which are the same as those shown in FIGS. 1A to 1C and thus the same reference numbers are used for these features. As in the previous embodiment, the second sensor system comprises a housing 110 within which a sensor 12, a pump 14 and a sorbent 16 are located. In this arrangement, a heater 50 is positioned adjacent the sorbent to improve the drying of the fluid. As explained in more detail below, the heater 50 is an optional extra to provide additional benefits in this arrangement but it will be appreciated that it may also be optionally included in the other arrangements to improve the drying efficacy of the sorbent.

In this arrangement, flow through the external aperture 18 into the housing 110 is controlled by a one way valve 120. The housing 110 comprises two (not three) chambers: a combined sensing and drying chamber 130 and a flow chamber 134 with flow between chambers being through an internal aperture 126. There is no valve on this aperture but one could optionally be included. The arrangement of the sorbent and the internal aperture 226 is such that fluid flows through the sorbent when exiting the flow chamber 134. The housing 110 also has an external venting aperture 40 through which fluid can exit the housing 110 via the flow chamber 134. A second one-way valve 42 is used to control flow through this external venting aperture 40 which may also be termed an exit aperture.

FIG. 2A shows a loading phase of operation for the sensing system. The pump 14 is set at maximum or at least a high rate above to ensure that the magnitude of the pressure differential between internal and external pressure is above a predetermined threshold value to reduce the pressure within the sensing and drying chamber relative to the pressure of the fluid outside the housing. The reduction in pressure is sufficient to cause the external valve 120 to open to allow a fluid sample to enter the housing 110 as indicated by the arrow. In this arrangement, the fluid sample (which is typically ambient air) is drawn into the sensing and drying chamber 130 of the housing 110. Once the required sample has been captured, the pump speed is reduced and the sensing system switches to the measurement phase shown in FIG. 2B. It is noted that as shown in FIG. 2A, the external venting valve 42 is configured to remain closed to ensure that there is the necessary pressure drop in the sensing and drying chamber 130.

As shown in FIG. 2B, the external valve 120 is closed. The pump 14 operates at a lower speed than that used in the loading phase to drive circulation of the fluid within the housing. Fluid flows in a measurement circulation path or sensing fluid path through the sensor 12, through the pump 14 and back into the sensing and drying chamber 130 through the internal aperture 126. The fluid also flows through the sorbent 16 on each measurement circulation path. Nevertheless, the fluid sample can be circulated through the sensor multiple times allowing measurement by averaging techniques as in the previous arrangement.

Once sufficient measurements have been captured or after a predefined time interval, the sensor system can be configured to operate in an optional regeneration phase as shown in FIG. 2C. In this arrangement, this is achieved by pulsing the flow direction for the pump 14 backwards and forwards and simultaneously activating the heater 50. Activation of the heater 50 drives water (or other adsorbed or absorbed substances) from the sorbent material. The rate at which water is released may effect the rate and even the direction of fluid flow within the housing. Accordingly, the temperature of the sorbent may be used to control the rate of flow and possibly also the direction of flow within the housing 110. When the flow direction of the pump is reversed, this reduces the pressure in the flow chamber 134 relative to the pressure in the sensing and drying chamber 130 which opens the second one-way valve 42 on the external venting aperture 42. As shown by the arrows, the fluid flows in a venting path (or regeneration path) from the sensor 12 through the sorbent 16, then through the internal aperture 126 into the flow chamber 134 and out of the housing 110 through the external venting aperture 40. The opening of the venting aperture 40 ensures that any substance which is removed from the sorbent is vented from the housing rather than recirculated within the housing. Alternatively, the pump is driven in a forward direction so that the flow path is the same as that indicated by arrows in FIG. 2B.

The regeneration phase is optional. This arrangement is simpler than the one shown in FIGS. 1A to 1C but still achieves improvements in the longevity of the sensor due to the optional regeneration phase. The control of the valve on the exit aperture also assists in controlling the fluid flows and pressures within the system.

Figure 3A:
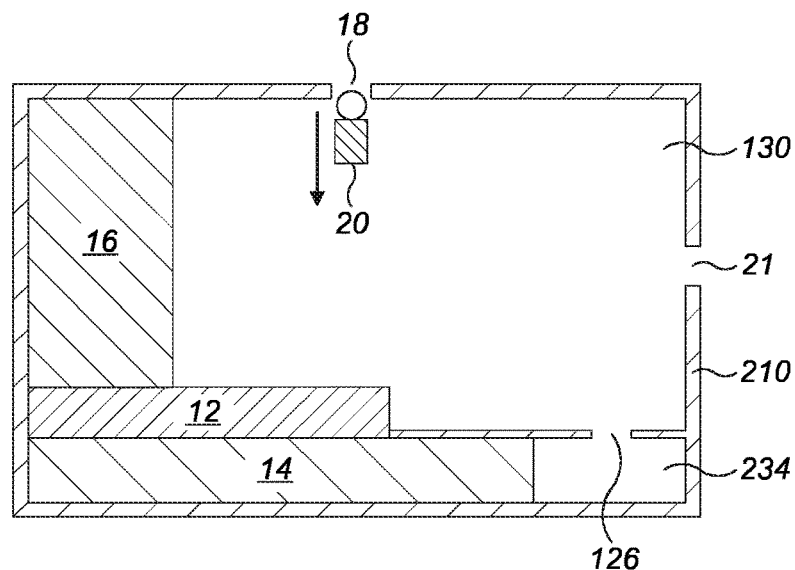
FIGS. 3A to 3C show a third sensor system in three different phases of operation.
Figure 3B:
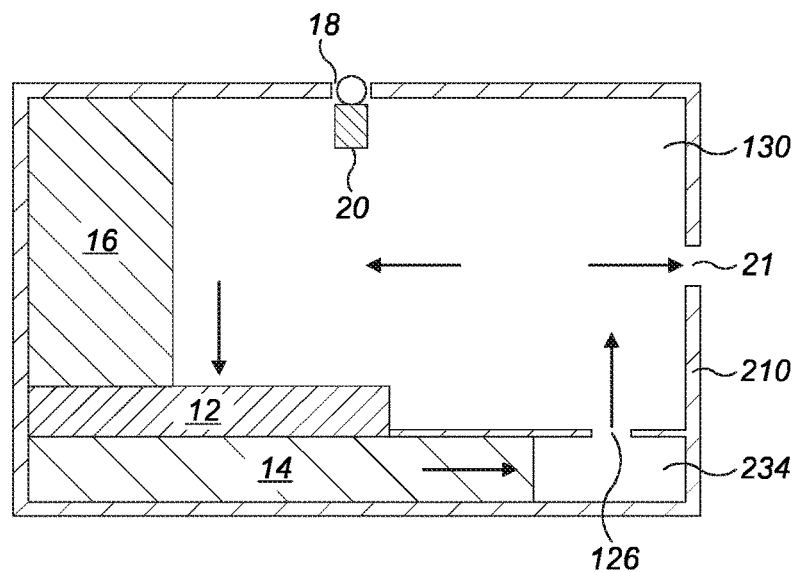
Figure 3C:
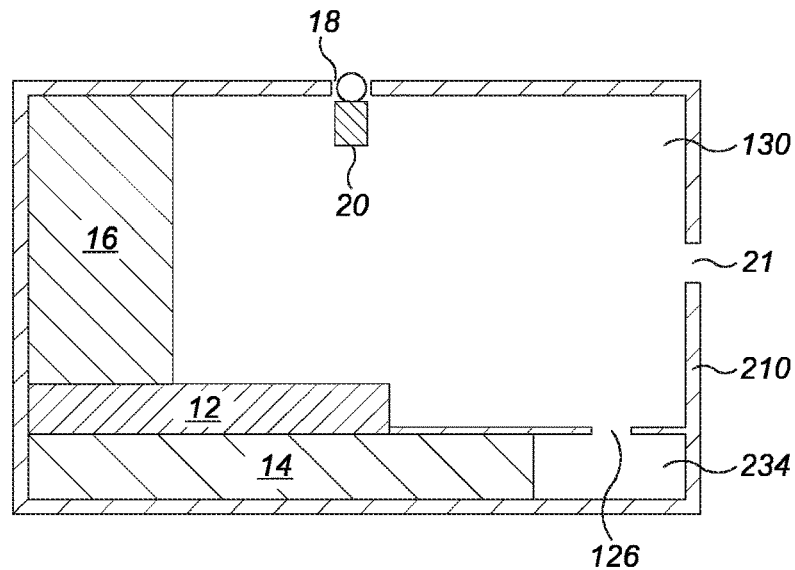

FIGS. 3A to 3C show a third sensor system having many features which are the same as those shown in FIGS. 1A to 2C and thus the same reference numbers are used for these features. As in the previous embodiments, the second sensor system comprises a housing 210 within which a sensor 12, a pump 14 and a sorbent 16 are located.

In this arrangement, flow through the external inlet aperture 18 into the housing 210 is controlled by a valve 20 similar to that used in FIGS. 1A to 1C and flow out of the housing is through a diffusion limited exit aperture 21. Like FIGS. 2A to 2C, the housing 210 comprises two (not three) chambers: a combined sensing and drying chamber 130 and a flow chamber 234 with flow between chambers being through an internal aperture 226. There is no valve on this aperture but one could optionally be included. In this arrangement, the sorbent is adjacent the sensor 12. As explained below, this is not the only suitable arrangement.

FIG. 3A shows a loading phase of operation for the sensing system. The pump 14 is set at maximum or at least a rate above a predetermined threshold value to reduce the pressure within the sensing and drying chamber relative to the pressure of the fluid outside the housing. The reduction in pressure is sufficient to cause the external valve 20 to open to allow a fluid sample to enter the housing as indicated by the arrow. In this arrangement, the fluid sample (which is typically ambient air) is drawn into the sensing and drying chamber 130 of the housing 210. Once the required sample has been captured, the pump speed is reduced and the sensing system switches to the measurement phase shown in FIG. 3B.

As shown in FIG. 3B, the external valve 20 is closed. The pump 14 operates at a lower speed than that used in the loading phase to drive circulation of the fluid within the housing. Fluid flows in a measurement circulation path through the sensor 12, through the pump 14 into the flow chamber 234 and back into the sensing and drying chamber 130 through the internal aperture 126. The fluid does not flow through the sorbent 12 on each measurement circulation path but as shown passes to one side of the sorbent 12. It is thus essential that the sorbent 12 is placed outside of the measurement circulation path. In this arrangement, this is achieved by placing the sorbent adjacent the sensor to one side of the housing but other arrangements could achieve the necessary separation from the circulation path. It is important that there is little drying in this measurement phase so the fluid sample can be circulated through the sensor multiple times allowing measurement by averaging techniques as in the previous arrangement.

Once sufficient measurements have been captured or after a predefined time interval, the sensor system can be configured to operate in a drying mode shown in FIG. 3C. The pump is off or only providing a low flow and thus there is no forced circulation path. Instead the fluid diffuses through the chambers within the housing. Accordingly, there is diffusive drying of the fluid by the sorbent 12. The external valve 20 remains closed in the drying phase. This may also be termed a rest phase because the pump 14 is generally off.

This arrangement is simpler than the ones shown in FIGS. 1A to 2C but still achieves improvements in the longevity of the sensor due to the drying phase. Like the other arrangements, the external valve 20 to the diffusion limited aperture 18 can be opened and closed quickly to allow control of the sample taken into the housing.

Figure 4A:
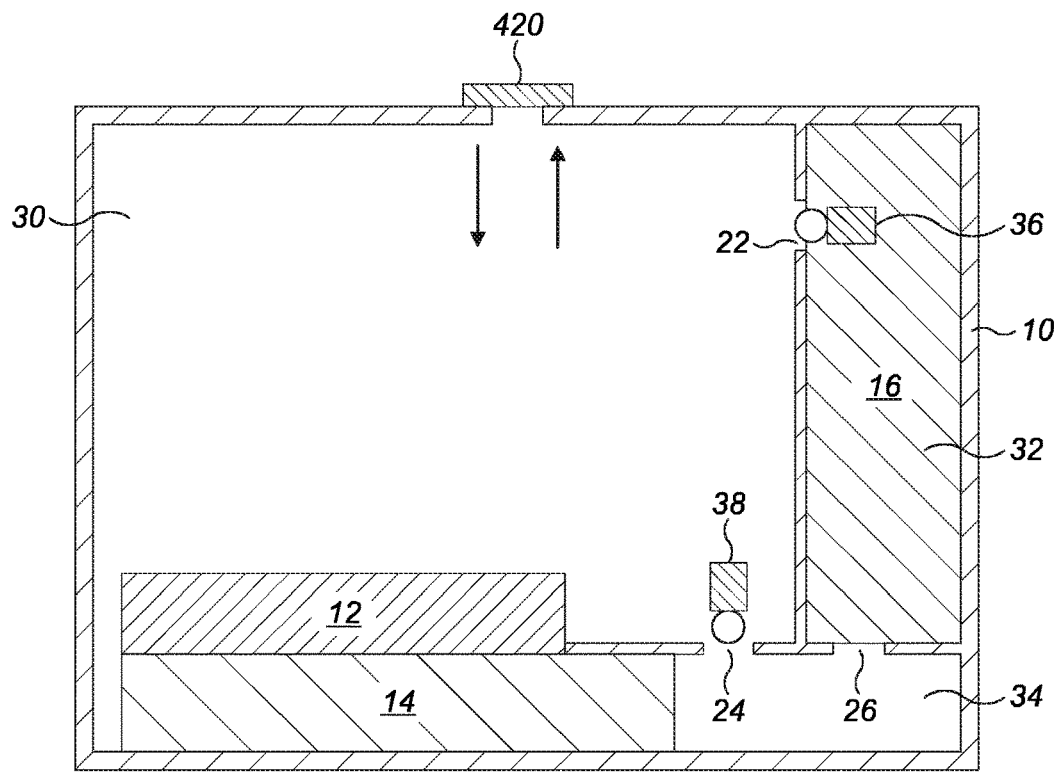
FIGS. 4A to 4C show three variations of sensor system.
Figure 4B:
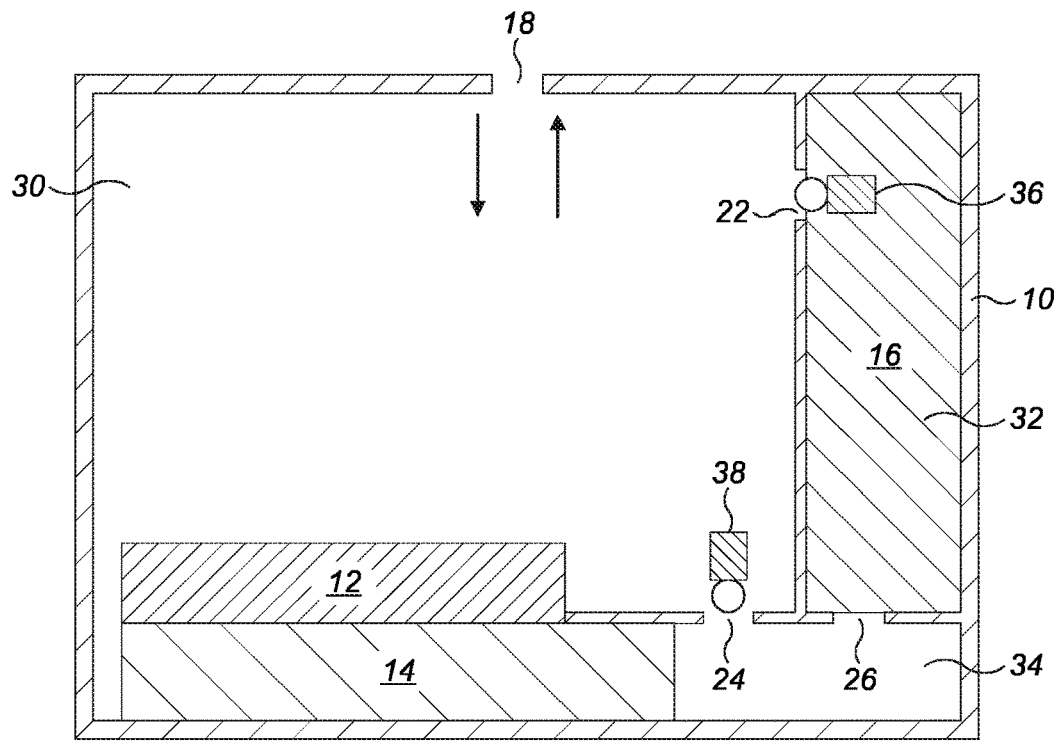
Figure 4C:
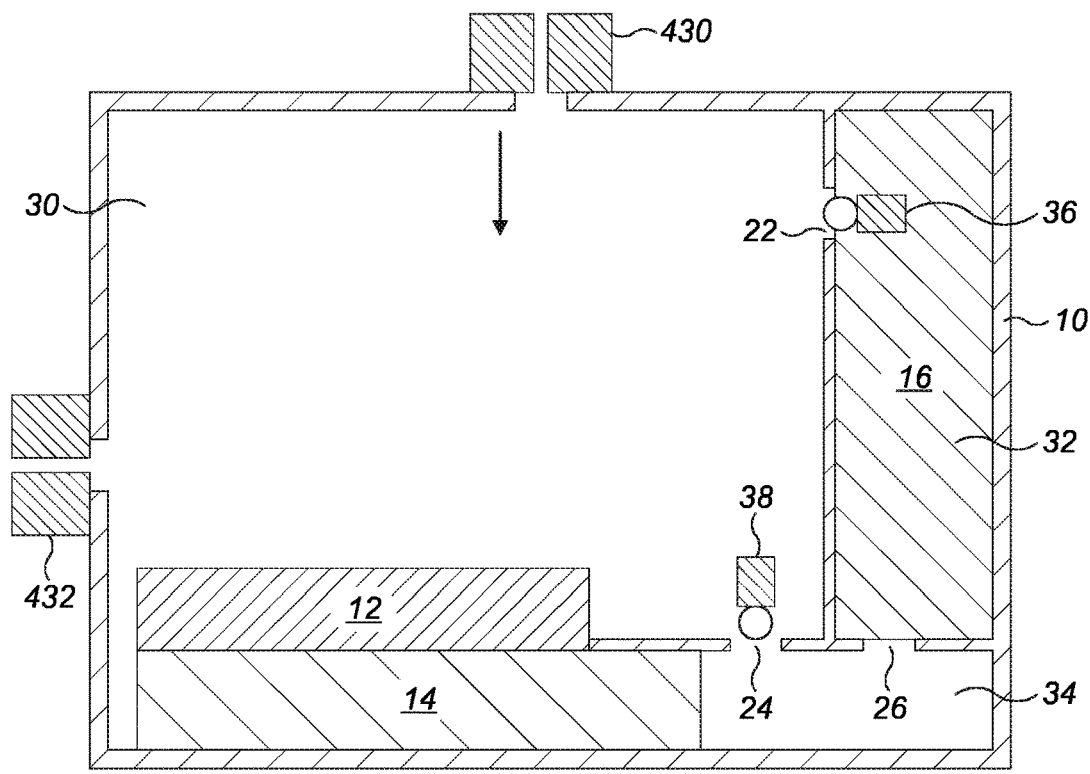

FIGS. 4A to 4C show variations of the embodiments of FIGS. 1A to 1C. It will be appreciated that the variations shown in FIGS. 4A to 4C may also be incorporated in the other embodiments. The same reference numbers are used for the features in common and thus as in all the previous embodiments, the system comprises a housing 10 within which a sensor 12, a pump 14 and a sorbent 16 are located.

FIG. 4A differs from the embodiment of FIG. 1A in that there is no one-way valve but instead a membrane 420 which covers the external aperture. The membrane 50 is made from a suitable material which controls diffusion through the external aperture both into the housing 10 and out of the housing 10. Thus the external aperture 18 operates as both an inlet and an exit aperture. Accordingly, there is no need for a second external aperture. The membrane 50 may be heated by a heat source (not shown) to control the rate of diffusion through the membrane 420 in one or both directions. It will be appreciated that the membrane 420 could sit within the aperture 18 as an alternative to covering the aperture 18 so that effectively the membrane 420 replaces the aperture 18.

FIG. 4B is similar to FIG. 4A except that there is no membrane over the external aperture 18. In this arrangement, the external aperture is a diffusion limited aperture which allows flow into and out from the housing. Thus, like FIG. 4A, the external aperture is both an inlet and an exit aperture. It will be appreciated that in FIGS. 4A and 4B more than one external aperture can be used if this is appropriate.

FIG. 4C differs from the embodiment of FIG. 1A in that differential lock caps 430, 432 are used on both the inlet and outlet apertures to control flow into and out from the housing. The differential lock caps may be the same or may be specifically designed for different operation depending on whether they are on the inlet or the outlet aperture.

In each of FIGS. 4A to 4C, although there is no valve, the operation of each system may be similar to that of the embodiment of FIG. 1A. There is thus a loading phase in which the pump 14 is driven to cause a pressure drop within the housing 10. In each embodiment, this causes a sample (or plug) of fluid to be drawn into the housing 10 so that in other words, fluid enters the housing 10 at a higher rate than the rate allowed by through normal diffusion through the membrane 420, aperture 18 or differential lock caps 430. The pump is then driven at lower speed in the measurement and drying phases with the direction of flow in the drying phase being the opposite of that in the measurement phase.

Alternatively, the entry of the sample into the housing 10 may be controlled by the membrane 420, the diffusion limited aperture 18 or the lock cap alone 430. In this case, the membrane 420, the diffusion 18 limited aperture or the lock cap 430 are effectively acting as a circulation means.

Figure 5A:
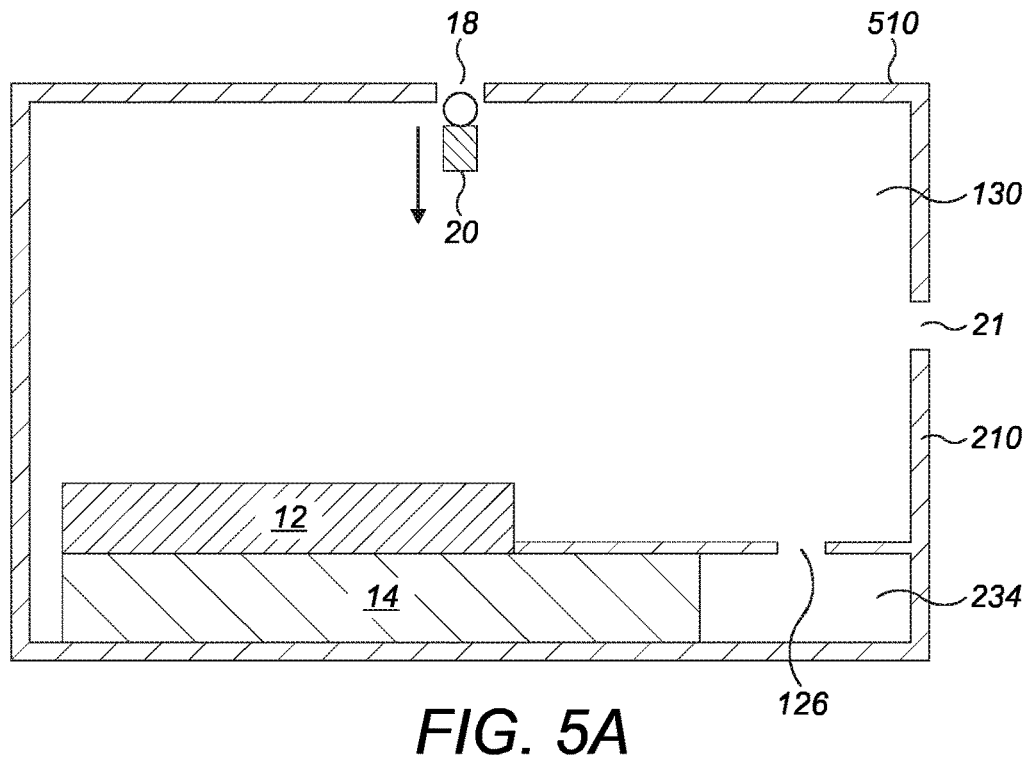
FIG. 5A shows another sensor system.
Figure 5B:
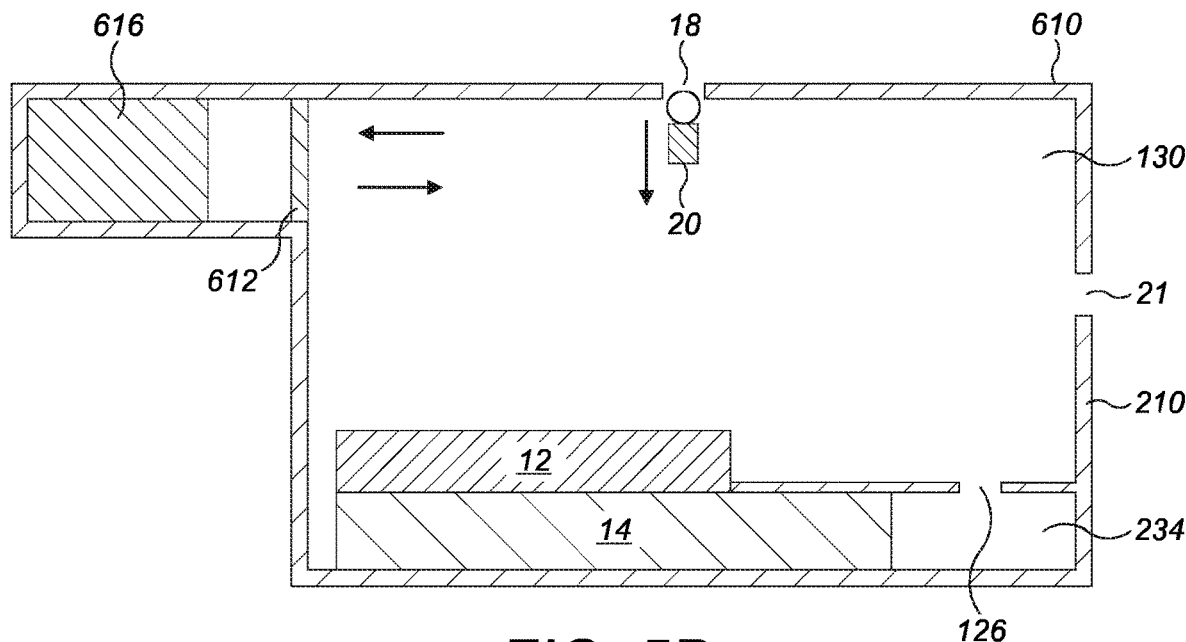
FIGS. 5B and 5C show an alternative sensor system in two phases of operation.
Figure 5C:
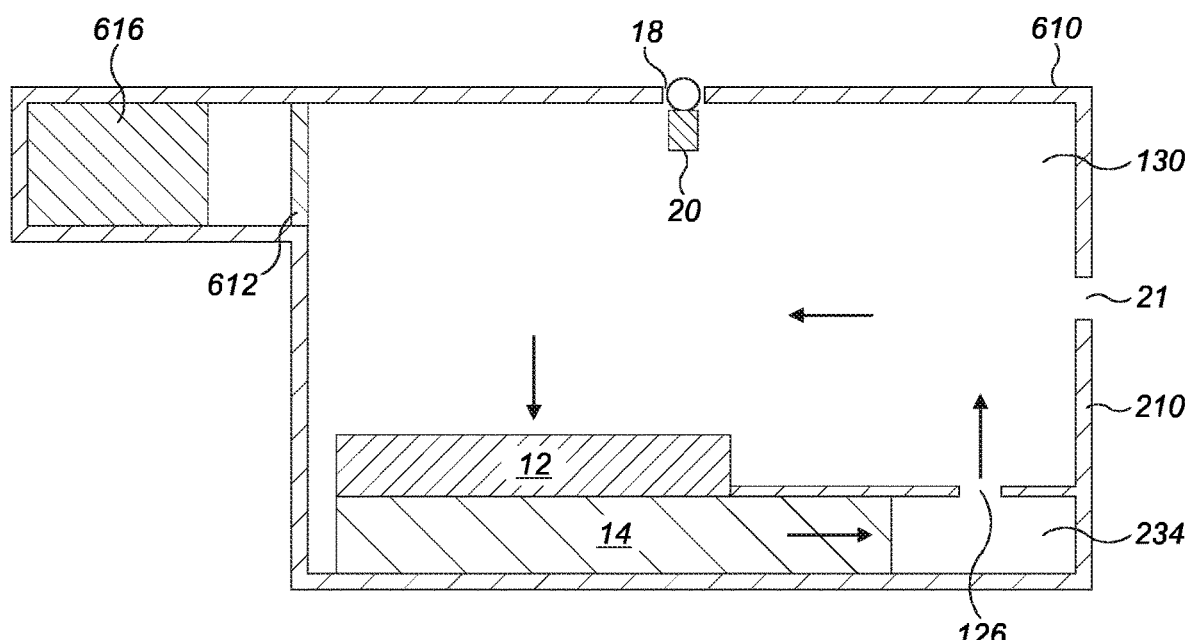

FIGS. 5A to 5C show variations of the embodiments of FIGS. 3A to 3C. It will be appreciated that the variations shown in FIGS. 5A to 5C may also be incorporated in the other embodiments. The same reference numbers are used for the features in common.

In FIG. 5A, the system comprises a housing 510 within which a sensor 12 and a pump 14 are located. In this system the housing 510 comprises internal walls (or a coating) which are formed from a sorbent material. Accordingly, there is no need for a separate block of sorbent material as in the previous embodiment. The sorbent material is thus integrated into the housing itself. The operation of the embodiment is otherwise unchanged and thus the sorbent walls will absorb or adsorb water in the drying mode when there is no or a very low flow. It will be appreciated that a separate sorbent block can also be removed from the other embodiments, for example by making the internal walls of the drying chamber in FIGS. 1A to 1C from a sorbent material or making the internal walls of the sensing and drying chamber in FIGS. 2A to 2C from a sorbent material.

In FIGS. 5B and 5C, the system comprises a housing 610 within which a sensor 12, a pump 14 and a conditioning material 616 are located. The conditioning material 616 may be a sorbent material as shown in FIGS. 1A to 5A. Alternatively, the conditioning material 616 may release water or another substance. It will be appreciated that in each of the embodiments of FIGS. 1A to 5A, the sorbent material could be replaced with a material which releases a substance. The conditioning material 616 is contained within a conditioning chamber in which the fluid drawn into the housing is conditioned (i.e. substance is removed or added).

As shown in FIG. 5B, the valve 20 is open and fluid flows into the housing 610 through the aperture 18 and into the conditioning material 616 in the conditioning chamber. The rate of flow into the conditioning chamber 616 may be controlled by the flow rate into the housing 610. Alternatively, or additionally an optional valve 612 may be used to control flow into the conditioning chamber. FIG. 5C shows an alternative fluid path in which sensing occurs. As shown in FIG. 5c, the valve 20 is closed.

Figure 6A:
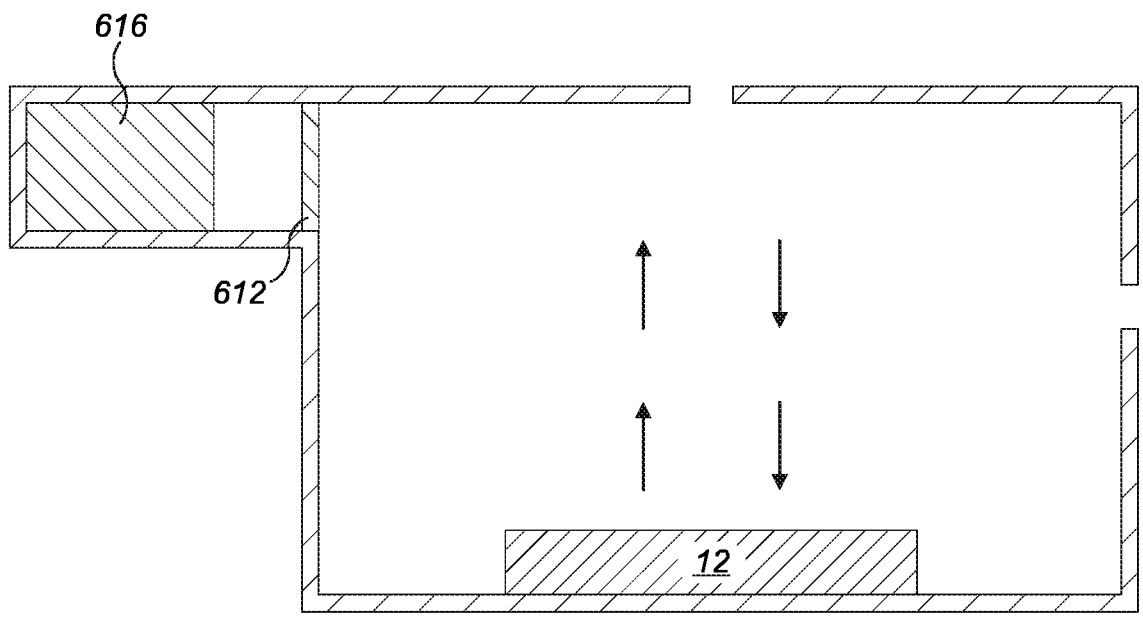
FIGS. 6A and 6B show a final sensor system in two phases of operation.
Figure 6B:
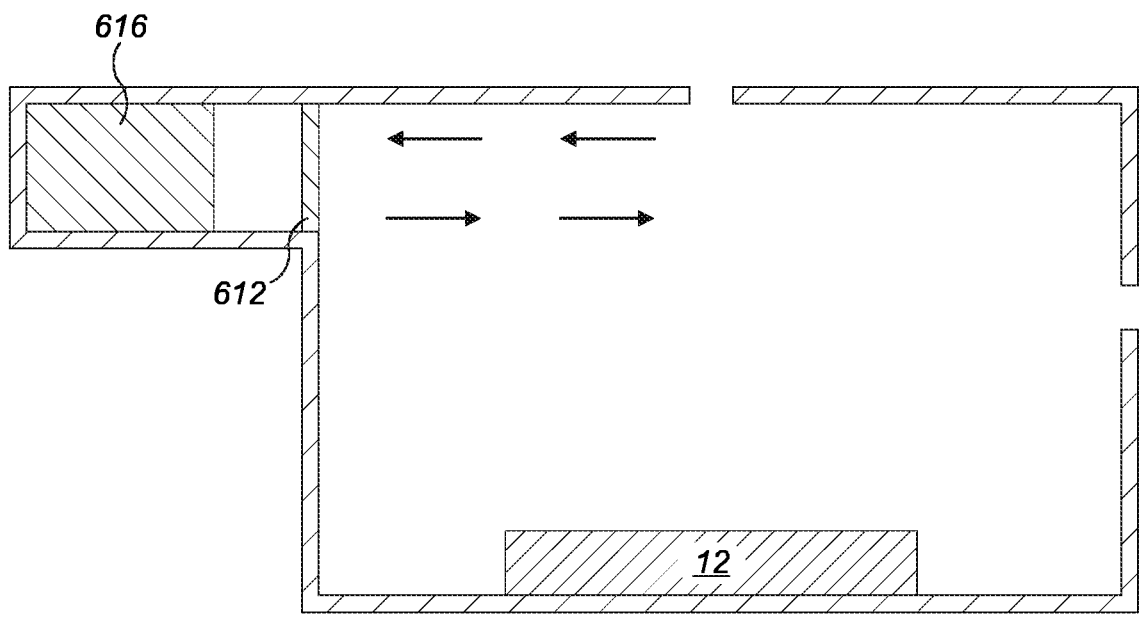

FIGS. 6A and 6B show a variations of the embodiments of FIGS. 5B to 5C. It will be appreciated that the variations shown in FIGS. 6A and 6B may also be incorporated in the other embodiments. The same reference numbers are used for the features in common. In this embodiment, there is no pump acting as the circulation means.

In FIGS. 6A and 6B, the system comprises a housing 610 within which a sensor 12, and a conditioning material 616 are located. The conditioning material 616 may be a sorbent material or may release water or another substance as previously described. As in the previous embodiment, the conditioning material 616 is contained within a conditioning chamber in which the fluid drawn into the housing is conditioned (i.e. substance is removed or added).

As shown in FIG. 6A fluid flows into the housing 610 and into the sensing fluid path in which sensing occurs. As shown in FIG. 6B, fluid flows into the housing 610 through the aperture 18 and into the conditioning material 616 in the conditioning chamber. The fluid path (i.e. the sensing fluid path of FIG. 6A or the conditioning fluid path of FIG. 6B) can be selected by controlling the rate of diffusion along each path. One variable which can be used to control the rate of diffusion is the diffusion rate through the inlet aperture 18. This can be controlled for example by using a membrane covering or mounted within the aperture 18. The membrane may have a variable diffusion rate depending on its temperature. For example at a first temperature, the diffusion rate may be high so that the fluid flows in the sensing fluid path and at a second temperature, the diffusion rate may be low so that the fluid flows in the conditioning fluid path. In such an arrangement, the circulation means may be the membrane.

Alternatively or additionally, the rate of flow into the conditioning chamber may be controlled by the use of a valve or a membrane 612 over the aperture into the conditioning chamber or by the use of a diffusion limited aperture (pinhole aperture). For example, the membrane may have a variable diffusion rate depending on its temperature so that at a first temperature, the diffusion rate may be high so that the fluid flows in the circulation fluid path and at a second temperature, the diffusion rate may be low so that the fluid flows in the sensing fluid path. In such an arrangement, the circulation means may be the valve, conditioning chamber valve, membrane and/or aperture. The shape of the conditioning chamber may also be used to control the diffusion rate, for example the size of the chamber may be variable to increase or decrease the distance from the inlet to the sorbent to adjust the diffusion rate to the sorbent. For example, at a first shorter length, the diffusion rate may be high so that the fluid flows in the circulation fluid path and at a second longer length, the diffusion rate may be low so that the fluid flows in the sensing fluid path. In such an arrangement, the circulation means may be the mechanism controlling the shape of the conditioning chamber.

Alternatively or additionally, the rate of flow may be adjusted by changing the distance between the inlet and the sensor. For example, at a first shorter length, the diffusion rate may be high so that the fluid flows in the sensing fluid path and at a second longer length, the diffusion rate may be low so that the fluid flows in the conditioning fluid path. In such an arrangement, the circulation means may be the mechanism controlling the distance between the inlet and the sensor.

Although a few preferred embodiments of the present invention have been shown and described, it will be appreciated by those skilled in the art that various changes and modifications might be made without departing from the scope of the invention, as defined in the appended claims.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:
1. A sensor system, comprising:
a housing having an inlet aperture through which a fluid enters the housing;
a conditioning material in the housing, the conditioning material being adapted to control levels of a substance within the housing;
a sensor for analysing the fluid in the housing; and
a circulation means configured to alternate circulation of the fluid within the housing between a sensing fluid path in which the fluid is analysed by the sensor and a second fluid path in which the fluid flow is conditioned, wherein the housing has a flow chamber which houses the circulation means, a second chamber which houses the sensor and a first internal aperture between the flow chamber and the second chamber.

2. The sensor system of claim 1, wherein the conditioning material is a sorbent material and the second fluid path is a drying path in which the fluid is dried by the sorbent material.

3. The sensor system of claim 2, wherein the sorbent material is located in the housing so that the fluid flows through the sorbent material in the drying path.

4. The sensor system of claim 1, wherein the housing has an exit aperture through which the fluid exits the housing, and the second fluid path is a regeneration path with fluid flow through the exit aperture.

5. The sensor system according to claim 1, wherein the circulation means is configured for bi-directional operation and altering a direction of operation of the circulation means alternates circulation of fluid within the housing between the sensing fluid path and the second fluid path.

6. The sensor system of claim 1, wherein the circulation means is configured to alternate circulation fluid by switching to a rest phase to circulate the fluid in the second fluid path.

7. The sensor system according to claim 1, wherein the inlet aperture is a diffusion limited aperture.

8. The sensor system according to claim 1 wherein the second chamber is a sensing chamber and the housing further comprises a conditioning chamber which houses the conditioning material.

9. The sensor system according to claim 8, further comprising a second internal aperture between the flow chamber and the sensing chamber and a third internal aperture between the conditioning chamber and the sensing chamber.

10. The sensor system according to claim 9, further comprising internal valves to control flow through the second and third internal apertures, wherein the circulation means is configured to control opening and closing of the internal valves.

11. The sensor system according to claim 1, wherein the sensor is configured to analyse the fluid using averaging techniques.

12. A method for analysing fluid in a housing using a sensor, the method comprising:
    drawing the fluid into the housing through an inlet aperture;
    selecting a fluid path within the housing, wherein the fluid path is selected from a sensing path, in which the fluid flows through the sensor to be analysed, and a second fluid path;
    circulating the fluid within the selected fluid path using a circulation means located within the housing, wherein the circulation means is configured for bi-direction operation, and said circulating the fluid within the selected fluid path includes selecting a direction of operation of the circulation means which drives the fluid in the selected fluid path;
    analysing the fluid within the housing using the sensor when the fluid is flowing in the sensing path; and
    controlling a level of a substance within the fluid using a conditioning material located within the housing when the fluid is flowing in the second fluid path.

13. The method of claim 12, wherein the second fluid path is a drying path, and said controlling a level of a substance includes removing the substance by drying the fluid using a conditioning material which is a sorbent material.

14. The method of claim 12, wherein the second fluid path is a regeneration path, and said controlling a level of a substance includes removing the substance by opening an exit aperture to permit fluid flow through the exit aperture.

15. The method of claim 14, wherein the conditioning material is a sorbent material, and the method further comprises heating the sorbent material when the fluid is flowing in the regeneration path to remove the substance from the sorbent material.

16. The method of claim 12, wherein circulating the fluid within the second fluid path comprises operating the circulation means in a rest phase.

17. The method of claim 12, further comprising circulating the fluid in the second fluid path before circulating the fluid in the sensing path.

18. A sensor system, comprising:
    a housing having an inlet aperture through which a fluid enters the housing;
    a conditioning material in the housing, the conditioning material being adapted to control levels of a substance within the housing;
    a sensor for analysing the fluid in the housing; and
    a circulation means configured to alternate circulation of the fluid within the housing between a sensing fluid path in which the fluid is analysed by the sensor and a second fluid path in which the fluid flow is conditioned,
    wherein the circulation means is located adjacent to the sensor forming a sealed path between the circulation means and the sensor.

19. The sensor system according to claim 1, wherein the second chamber houses the conditioning material.

* * * * *